United States Patent [19]

Reading et al.

[11] Patent Number: 4,927,502

[45] Date of Patent: May 22, 1990

[54] METHODS AND APPARATUS USING GALVANIC IMMUNOELECTRODES

[75] Inventors: Christopher L. Reading, Kingwood, Tex.; Malcolm R. Smyth; Richard O'Kennedy, both of Dublin, Ireland

[73] Assignee: Board of Regents, The University of Texas, Austin, Tex.

[21] Appl. No.: 304,739

[22] Filed: Jan. 31, 1989

[51] Int. Cl.$^5$ .......................................... G01N 27/50
[52] U.S. Cl. ............................... 204/153.1; 128/635; 204/403; 435/7; 435/291
[58] Field of Search .................... 435/7, 291; 204/403, 204/1 T; 128/635

[56] References Cited

U.S. PATENT DOCUMENTS

| | | | |
|---|---|---|---|
| 3,975,238 | 8/1976 | Bean et al. | 435/4 |
| 4,020,830 | 5/1977 | Johnson et al. | 204/418 X |
| 4,072,576 | 2/1978 | Arwin et al. | 435/7 |
| 4,151,049 | 4/1979 | Janata | 704/1 T |
| 4,238,757 | 12/1980 | Schenck | 357/25 |
| 4,334,880 | 6/1982 | Malmros | 436/501 |
| 4,402,819 | 9/1983 | Rechnitz et al. | 204/418 |
| 4,444,892 | 4/1984 | Malmros | 436/528 |
| 4,562,157 | 12/1985 | Lowe et al. | 435/291 |
| 4,591,550 | 5/1986 | Hafeman et al. | 435/4 |
| 4,592,894 | 6/1986 | Panitz | 422/69 |

FOREIGN PATENT DOCUMENTS

| | | |
|---|---|---|
| 0125139A2 | 11/1984 | European Pat. Off. |
| 0150999A2 | 8/1985 | European Pat. Off. |
| 0155193A2 | 9/1985 | European Pat. Off. |
| 0167248A2 | 1/1986 | European Pat. Off. |
| 208753 | 8/1988 | Japan |

OTHER PUBLICATIONS

N. Yamamoto, et al., "Antigen—Antibody Reaction Investigated with Use of a Chemically Modified Electrode", Clinical Chemistry vol. 26, No. 11, at 1569–1572 (1980).
G. Robinson et al., "Bioelectrochemical Immunoassay for Human Chorionic Gonadotrophin in Serum Using an Electrode—Immobilized Capture Antibody", Biosensors, vol. 2, at 45–57 (1986).
Rogers, et al., Immunosensors Based on Acoustic, Optical and Bioelectrochemical Devices and Techniques, The British Food Manufacturing Industries Research Association, Technical Notes, No. 49, Oct. 1986.
M. Meyerhoff et al., "Antibody Binding Measurements with Hapten—Selective Membrane Electrodes", Science, vol. 195, at 494–495 (Feb. 4, 1977).
S. Suzuki et al., "Bioelectrochemical Sensors Based on Immobilized Enzymes, Whole Cells, and Proteins", Applied Biochemistry and Bioengineering, vol. 3, at 145–147 (1981).
J. Boitieux, et al., "An 'Antibody Electrode', Preliminary Report of a New Approach in Enzyme Immunoassay", Clin. Chem., vol. 25, No. 2, at 318–321 (1979).
M. Keating et al., "Potentiometric Digoxin Antibody Measurements with Antigen–Inophore Based Membrane Electrodes", Anal. Chem., vol. 56, No. 4, at 801–806 (1984).
G. Guilbault, "Immobilized Biological and Immuno Sensors", Anal. Proc., vol. 20, at 550–552 (Nov. 1983).
N. Yamamoto et al., "Potentiometric Investigations of Antigen–Antibody and Enzyme–Enzyme Inhibitor Reactions Using Checically Modified Metal Electrodes", J. of Immunol. Methods, vol. 22, at 309–317 (1978).
N. Yamamoto et al., "The Electrical Method of Investigation of the Antigen–Antibody and Enzyme–Enzyme Inhibitor Reactions Using Chemically Modified Electrodes", Chemistry Letters at 245–246 (1978).

Primary Examiner—G. L. Kaplan
Attorney, Agent, or Firm—Arnold, White & Durkee

[57] ABSTRACT

Methods and apparatus for detecting immunochemical reactions and levels of antigens and antibodies in serum. A selected immunochemical reactant is bound to the surface of a first electrode. A second electrode is provided such that the electrodes generate a galvanic current when electrically interconnected and immersed in conductive aqueous solution. The electrodes are electrically interconnected and immersed into a conductive aqueous solution containing the complementary immunochemical reactant to the bound immunochemical reactant. The galvanic current generated by the immersed electrodes is measured as a function of time. The level of the complementary immunochemical reactant in the solution is calculated by comparing the measured current with a standard current.

22 Claims, 2 Drawing Sheets

METHODS AND APPARATUS USING GALVANIC IMMUNOELECTRODES

BACKGROUND OF THE INVENTION

This invention relates to methods and apparatus for detecting immunochemical reactions and measuring antigen and antibody levels in solution through the use of galvanic cell systems.

Galvanic cell systems involve placing two dissimilar metals (i.e. electrodes) in a conductive solution. When the two electrodes are connected by a wire, current is produced therethrough due to galvanic reactions at the electrodes. At one electrode (called the anode), the first metal ($M_1$) goes into solution to form metal ions, transferring electrons through the wire to the other electrode (called the cathode) according to the general formula:

$$M_1^o \leftrightarrow M_1^{+z} + ze^-$$

where z is the charge of the metal ion.

At the cathode, electrons are transferred from the cathode surface to metal ions in solution to form metal according to the general formula:

$$M_2^{+y} + ye^- \leftrightarrow M_2^o$$

where y is the charge on the metal ion in solution.

Current flow in the circuit can be measured with a conventional ammeter. With small electrodes, the current is generally on the order of microamps.

It is an object of the present invention to employ galvanic cell systems to detect immunochemical reactions and measure antigen and antibody levels in a conductive aqueous solution, such as serum, plasma, whole blood, or urine.

SUMMARY OF THE INVENTION

Accordingly, the present invention involves the preparation and use of galvanic immunoelectrodes for use in galvanic cell systems to detect immunochemical reactions and detect antigen or antibody levels in the conductive solution of the galvanic cell. The galvanic immunoelectrodes used in the present invention comprise conductive bodies with a selected antibody or antigen bound to the surface of one immunoelectrode in the galvanic system.

The electrodes used in the present invention may be metallic, or any other conductor or semiconductor.

The term "immunochemical reactant" will be used herein to mean either an antibody or an antigen. The term "complementary immunochemical reactant" will be used to mean the specific immunochemical counterpart to a selected immunochemical reactant. Thus, when a selected antibody is bound to an electrode in accordance with the present invention, then the term "complementary immunochemical reactant" means the complementary antigen to that bound antibody. In this embodiment, the invention provides a system for measuring the level of the complementary antigen in solution. Conversely, when a selected antigen is bound to an electrode in accordance with the present invention, then the term "complementary immunochemical reactant" means the specific antibody to that bound antigen. In this embodiment, the invention provides a system for measuring the level of the specific antibody in solution.

Thus, one aspect of the present invention provides a method for measuring the level of a complementary immunochemical reactant in a conductive aqueous solution. The conductive aqueous solution could be any biological fluid or test solution (e.g. medium from a fermentation process). A selected immunochemical reactant (i.e. an antibody or antigen) is bound onto a first electrode. The first electrode is preferably metallic, and a variety of metals may be used for this purpose. Preferably the first electrode comprises gold, cobalt, iron, silver, copper or solder. The term "solder" is meant to include mixtures of tin and lead, e.g. 60% tin and 40% lead. The first electrode with the selected immunochemical reactant bound to its surface is placed into a conductive aqueous solution along with a second electrode. The second electrode is made of a metal different from the first metal, so that a galvanic current is generated when the first and second electrodes are electrically interconnected and immersed in a conductive aqueous solution. The electrodes are electrically interconnected and immersed in a conductive aqueous solution containing the complementary immunochemical reactant to the bound immunochemical reactant. The galvanic current generated by the immersed electrodes as a function of time is measured, and the level of the complementary immunochemical reactant in the solution is measured.

It has been discovered by the inventors that when the solution being tested contains the complementary immunochemical reactant to the bound immunochemical reactant, the current measurement decreases rapidly with time. Without wishing to be bound by theory, the inventors postulate that this phenomenon is caused by "contamination" of the first electrode surface due to immunochemical reactions occurring between the immunochemical reactants at the surface of the first electrode. Electrode surfaces in galvanic cells have a "double electrical layer" which regulates the transfer of electrons to the metal surface, ionization at the metal surface, and transfer of metal atoms to/from the solution from/to the metal surface. Certain substances, such as proteins, appear to contaminate the electrodes and affect this double electrical layer. Thus, when an electrode surface is treated with an antibody or antigen, the bound antibody or antigen functions as a resistor, limiting the current flow. When an immunochemical reaction occurs on the surface of the electrode between the immobilized antibody or antigen and the specific counterpart in solution, an immunological complex further contaminates the double electrical layer of the electrode, and thus further resists the galvanic current flow.

Thus, the behavior of current flow with respect to time indicates the occurrence of immunochemical reactions occurring between the bound antibody or antigen and counterpart in a serum being examined. It has been found that when a galvanic electrode having a selected immunochemical reactant bound to its surface in accordance with the present invention is immersed into a conductive test solution containing the complementary immunochemical reactant to the bound immunochemical reactant, the galvanic current flow decreases much more rapidly than when the galvanic electrode is placed into a similarly conductive standard solution which does not contain the complementary immunochemical reactant. By measuring the current flow as a function of time of the two galvanic cells and comparing them, the level of complementary immunochemical reactant in the test solution can be calculated. This may be achieved by comparing the decrease in current obtained with the unknown test solution with that obtained when similar electrodes are placed in standard solutions containing known concentrations of the complimentary immunochemical reactant.

Thus, when a selected antibody is bound to the surface of an electrode in accordance with the present invention, the level of complementary antigen to the bound antibody in a test solution can be measured. Similarly, when a selected antigen is bound to the electrode, the level of specific antibody to the bound antigen in a test solution can be measured. For example, the integrated galvanic current over a specified time period can be measured by a conventional coulometer for the test solution and the standard solution and compared. The level of complementary immunochemical reactant in the test solution is then calculated by measuring the integrated galvanic current over specified time periods for a range of standard solutions of the immunochemical reactant. A standard curve is then constructed, and the concentration of the immunochemical reactant in the test solution can be calculated.

One can also measure the time required for the galvanic current flow to decrease to a specified level using both the test solution and the standard solution, and compare the two measurements. From this, the antigen or antibody level in solution can be derived. It has been found that the greater the concentration of the reactant, the shorter the time required for a specified decrease in galvanic current to occur.

Preferably, measurements with standard solutions are made prior to examination of the test solution and stored in a microcomputer for comparison. When this is done, solutions can be conveniently tested for antigen or antibody levels without preparation and measurement of standard solutions with each test solution.

Preferably, the selected immunochemical reactant is bound to the surface of the electrode in accordance with the present invention by immersing the electrode into a solution containing the reactant, the solution having a pH slightly higher than the isoelectric point of the immunochemical reactant to be bound. The binding is essentially irreversible at such conditions.

In accordance with another embodiment of the present invention, a device for measuring the level of a complementary immunochemical reactant in a conductive aqueous solution is provided. The device includes a first electrode having a selected immunochemical reactant bound to its surface. It also includes a second electrode, the electrodes generating a galvanic current when electrically interconnected and immersed in a conductive aqueous solution. The electrodes are electrically interconnected, for example, with a copper wire. A means for measuring the current generated by the electrodes as a function of time when immersed in a conductive aqueous solution is also provided. For example, an ammeter and time piece or a coulometer may be used.

Also, a means for comparing the measured galvanic current with a standard current and calculating the level of the complementary immunochemical reactant is provided. For example, the galvanic current measurements may be transferred to a microcomputer via an analog-to-digital converter and compared to similar measurements on standard solutions stored in the microcomputer. Preferably, the device also includes a means for displaying the calculated reactant level, such as a liquid crystal display (LCD) and driver.

BRIEF DESCRIPTION OF THE DRAWINGS

This invention is now described by reference to the appended drawings which illustrate particular preferred embodiments of the apparatus and methods provided by the present invention.

DETAILED DESCRIPTION OF PREFERRED EMBODIMENTS

Figure 1:
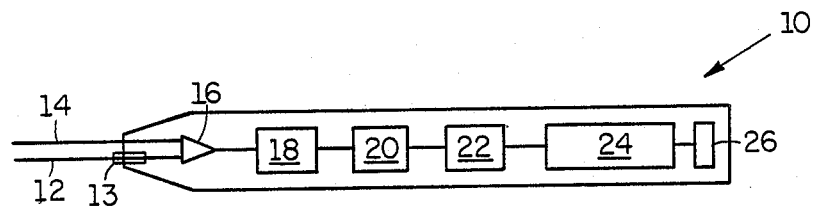
FIG. 1 is a schematic view of a device in accordance with a preferred embodiment of the present invention.

Referring to FIG. 1, a preferred embodiment of the present invention is shown, comprising a "ball point pen"-shaped immunodiagnostic instrument suitable for field application. The device or instrument 10 includes a first electrode 12 with a selected immunochemical reactant bound to its surface. For example, immobilized monoclonal antibody to the beta-subunit of human chorionic gonadotropin (B-HCG) may be bound to the first electrode 12, making the device 10 a convenient sensor for dipping into a urine sample for analysis of pregnancy. The first electrode 12 is preferably removable at plug 13 so that it may be discarded and replaced after use.

The instrument 10 further includes a second electrode 14 made of a metal different than the first electrode 12. The electrodes 12, 14 are electrically interconnected via a current sensitive transistor amplifier 16 where the integrated galvanic current is measured. This measurement is transferred via an analog-to-digital converter 18 to a processor 20. Integrated galvanic currents for standard solutions (i.e. solutions having similar conductivity to the antibody or test solution but containing no complementary immunochemical reactant to the antigen bound on electrode 12) are stored in processor 20 for comparison to measurements on the test solution. The level of complementary immunochemical reactant in the test solution calculated by the processor is transferred via an LCD driver 22 and displayed at the LCD 24. A battery 26 or other source is provided to power the components of the device 10.

In operation, the electrode 12, 14 are immersed into a test solution containing the complementary immunochemical to the antibody or antigen bound on the surface of electrode 12. The integrated galvanic current is measured by the amplifier 16 and transferred to the processor 20 via the analog-to-digital converter 18. The processor 20 calculates the level of complementary immunochemical reactant in the test solution by comparing the measured integrated current with integrated currents for standard solutions stored in the processor. The calculated antigen or antibody level is displayed on LCD 24.

Figure 2:
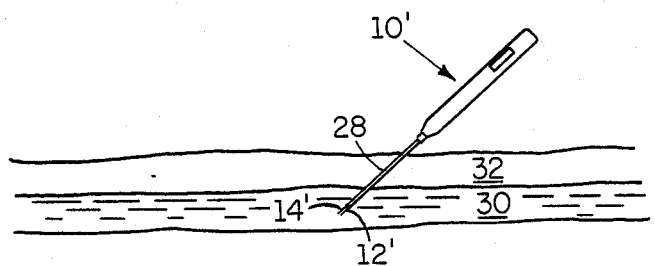
FIG. 2 is a schematic view of another preferred embodiment of the present invention.

Referring now to FIG. 2, another preferred embodiment is shown. Device 10' is similar to device 10 shown in FIG. 1, except that electrodes 12' and 14' are housed within a catheter 28. In this embodiment, electrodes 12' and 14' can be inserted directly into a blood vein or vessel 30 by puncturing skin 32 with the catheter 28. This embodiment provides the advantage of allowing constant monitoring of the level of a chemotherapeutic agent or drug being administered to a patient.

Figure 3:
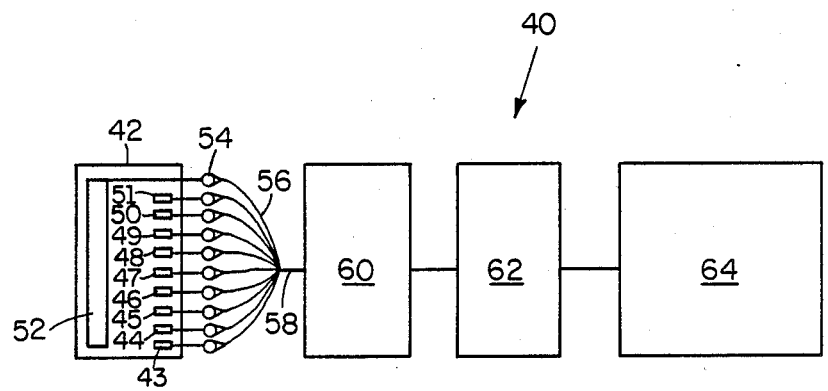
FIG. 3 is a schematic view of yet another preferred embodiment of the present invention.

Referring to FIG. 3, another preferred embodiment is illustrated. The apparatus 40 includes a disposable "cassette"-type serum tray 42. The serum tray 42 includes a plurality of first metallic electrodes 43-51. Each electrode 43-51 has a different immunochemical reactant bound to its surface. Each electrode 43-51 is electrically interconnected to a common metallic electrode 52 made of a second metal different from the first metal via electrical contacts 54 and wires 56 connected to a common lead 58. An amplifier 60 measures the integrated galvanic current generated between the common electrode 52 and each first metallic electrode 43-51. These measurements are transmitted to microcomputer 64 via an analog-to-digital converter 62. The microcomputer 64 calculates the level of each complementary immunochemical reactant corresponding to each antibody or antigen bound on electrodes 43-51 by comparison with standard currents as previously described in connection with FIGS. 1 and 2.

In operation, the tray 42 is filled with a conductive aqueous solution such that all the electrodes 43-52 are immersed. In this manner, the level of a plurality of complementary immunochemical reactants in the solution can be simultaneously calculated.

The following examples are designed to illustrate certain aspects of the present invention. However, they should not be construed as limiting the claims thereof.

EXAMPLE I

Figure 4:
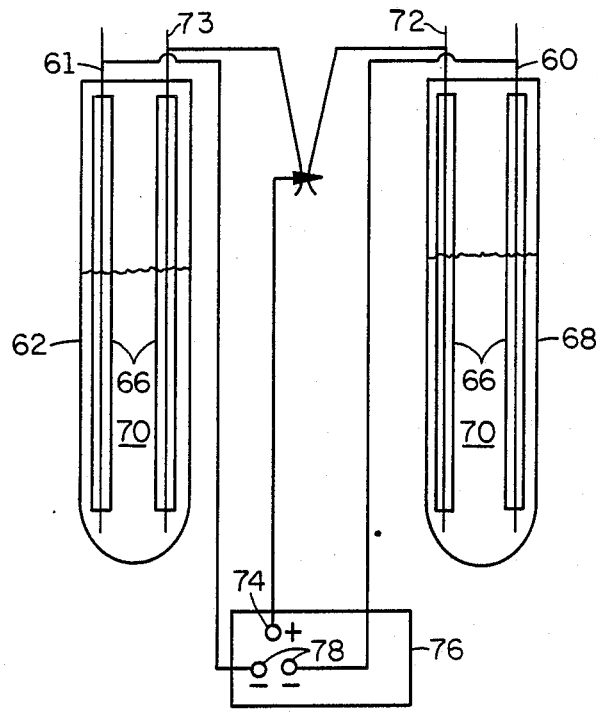
FIG. 4 is a schematic view of apparatus used in connection with Example I.

FIG. 4 illustrates the apparatus used in connection with the example described below. Two solder (60% tin, 40% lead) electrodes were first prepared by immersing in mouse immunoglobulin at 0.5 mg/ml in 0.05M sodium carbonate buffer pH 9.6 for 5 minutes and washed. This caused adsorption of the mouse immunoglobulin to the solder electrodes 60 and 61. A tube 62 containing fetal bovine serum 64 (used as a standard) was fitted with hollow tubing 66. A tube 68 containing donkey-anti-mouse antiserum 70 was similarly fitted with hollow tubing 66. Copper electrodes 72 and 73 were fitted into one of the pieces of tubing in the tubes 68 and 62, respectively. The copper electrodes 72 and 73 were connected to the positive lead 74 of the digital ammeter 76. The solder electrodes 60 and 62 with immobilized mouse immunoglobulin were washed in running water and inserted into the tubing 66, and connected to the negative leads 78 of the digital ammeter 76.

The instantaneous current flow was approximately 13 microamps, but decreased with time. The time for the current to decrease to 5 microamps was measured in replicates with three separate sets of solder electrodes 60 and 62. A tabulated summary of results is shown in Table 1. As an example of the difference seen in the specific response, the actual times for a decrease from 13 microamps to 5 microamps in the two measurements with electrode pair I were 45 and 49 seconds for fetal bovine serum and 5.8 and 6.4 seconds for donkey-anti-mouse serum.

By way of comparison, there was no difference between the times with the two sera if the solder electrodes did not have immobilized mouse immunoglobulin bound thereto.

TABLE 1

| Electrode pair | Number of measurements | Mean % decrease in time in the presence of specific antibody | Standard deviation |
|---|---|---|---|
| I | 2 | 87.1 | ±.07% |
| II | 7 | 93.3 | ±4.7% |
| III | 6 | 93.5 | ±6.3% |

From this data, the level of the specific antibody to mouse immunoglobulin can be calculated by comparison with values similarly obtained using solutions of known concentrations of mouse immunoglobulin.

The instant invention has been disclosed in connection with specific embodiments. However, it will be apparent to those skilled in the art that variations from the illustrated embodiment may be undertaken without departing from the spirit and scope of the invention.

What is claimed is:

1. A method for measuring the level of a complementary immunochemical reactant in a conductive aqueous solution, comprising the steps of:
   providing a first electrode and a second electrode, the electrodes having surfaces and generating a galvanic current when electrically interconnected and immersed in a conductive aqueous solution;
   binding a selected immunochemical reactant to the surface of the first electrode;
   electrically interconnecting the first and second electrodes;
   immersing the electrodes in a conductive aqueous solution containing the complementary immunochemical reactant to the bound immunochemical reactant;
   measuring the galvanic current generated by the immersed electrodes as a function of time;
   calculating the level of the complementary immunochemical reactant in the solution by comparing the measured current with a standard current;
   wherein the standard current substantially represents the galvanic current as a function of time generated by the electrodes when immersed in a standard solution, the standard solution being a solution having similar conductivity to the conductive aqueous solution and containing no complementary immunochemical reactant.

2. The method of claim 1, wherein the bound immunochemical reactant is an antibody, and the complementary immunochemical reactant is an antigen.

3. The method of claim 1, wherein the bound immunochemical reactant is an antigen, and the complementary immunochemical reactant is an antibody.

4. The method of claim 1, wherein the conductive aqueous solution is a serum.

5. The method of claim 1, wherein the conductive aqueous solution is plasma.

6. The method of claim 1, wherein the conductive aqueous solution is whole blood.

7. The method of claim 1, wherein the conductive aqueous solution is urine.

8. The method of claim 1, wherein the first electrode is an anode.

9. The method of claim 1, wherein the first electrode is a cathode.

10. The method of claim 1, wherein the first electrode comprises gold, cobalt, iron, silver, copper or solder.

11. A device for measuring the level of a complementary immunochemical reactant in a conductive aqueous solution, comprising:
- a first electrode having a surface and having a selected immunochemical reactant bound to its surface and a second electrode, the electrodes generating a galvanic current when electrically interconnected and immersed in a conductive aqueous solution;
- an electrical interconnection between the first and second electrodes;
- means for measuring the galvanic current generated by the first and second electrodes as a function of time when immersed in a conductive aqueous solution;
- means for comparing the measured galvanic current with a standard current and calculating the level of the complementary immunochemical reactant;
- wherein the standard current substantially represents the galvanic current as a function of time generated by the electrodes when immersed in a standard solution, the standard solution being a solution having similar conductivity to the conductive aqueous solution and containing no complementary immunochemical reactant.

12. The device of claim 11, further comprising means for displaying the level of complementary immunochemical reactant in the conductive aqueous solution.

13. The device of claim 11, wherein the bound immunochemical reactant is an antibody.

14. The device of claim 11, wherein the bound immunochemical reactant is an antigen.

15. The device of claim 11, further comprising a catheter housing the electrodes.

16. The device of claim 11, wherein the first metallic electrode comprises gold, cobalt, iron, silver, copper or solder.

17. The device of claim 11, wherein the first electrode is an anode.

18. The device of claim 11, wherein the first electrode is a cathode.

19. The device of claim 11, wherein the means for measuring the galvanic current as a function of time is a coulometer.

20. A device for measuring the level of a plurality of complementary immunochemical reactants in a conductive aqueous solution, comprising:
- a plurality of first electrodes, each first electrode having a surface and different immunochemical reactant bound to its surface, and a common electrode, each first electrode generating a galvanic current when electrically interconnected with the common electrode and immersed in a conductive aqueous solution;
- an electrical interconnection between each first electrode and the common electrode;
- means for measuring the galvanic current generated by each first electrode and common electrode as a function of time when immersed in a conductive aqueous solution;
- means for comparing each measured galvanic current with a standard current and calculating the level of each complementary immunochemical reactant to each bound immunochemical reactant;
- wherein the standard current substantially represents the galvanic current as a function of time generated by the electrodes when immersed in a standard solution, the standard solution being a solution having similar conductivity to the conductive aqueous solution and containing no complementary immunochemical reactants.

21. The device of claim 20, wherein each bound immunochemical reactant is a different antibody.

22. The device of claim 20, wherein each bound immunochemical reactant is a different antigen.

* * * * *